Figure 2:
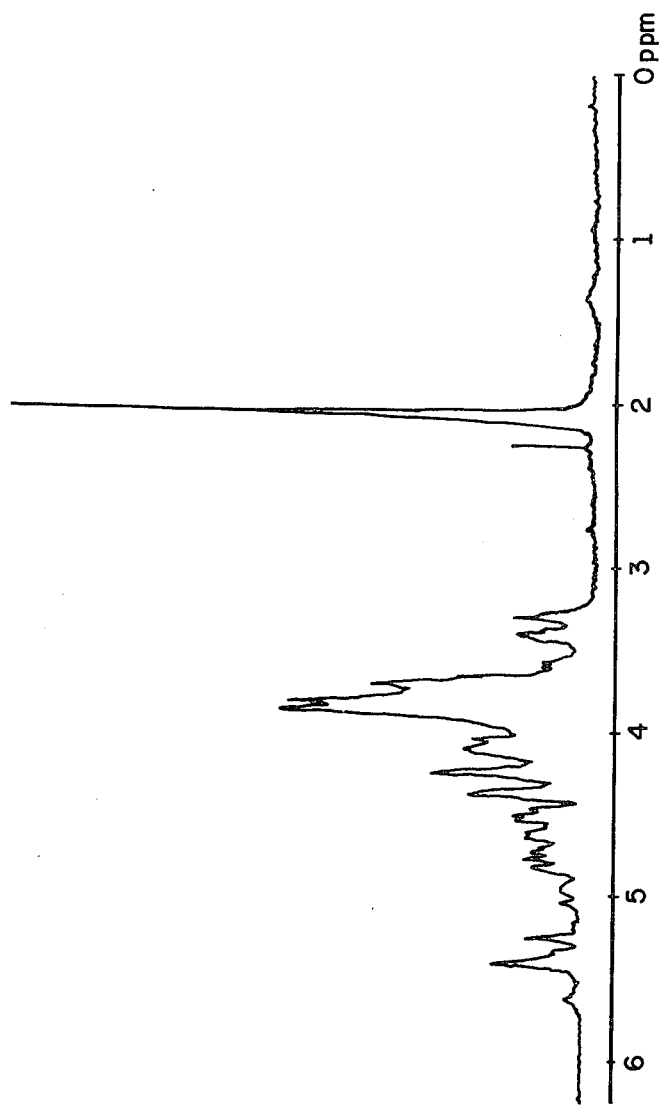

United States Patent [19]

Sanders et al.

[11] 4,438,108

[45] Mar. 20, 1984

[54] ANTI-THROMBOTICUM BASED ON POLYSACHARIDES, METHOD FOR ITS PREPARATION AND PHARMACEUTICAL COMPOSITIONS

[75] Inventors: Adrianus L. M. Sanders, Uden; Dirk G. Meuleman, Oss; Huibert C. T. Moelker, Megen; Gijsbert W. K. van Dëdem; François E. A. van Houdenhoven, both of Heesch, all of Netherlands

[73] Assignee: Akzo N.V., Arnhem, Netherlands

[21] Appl. No.: 377,581

[22] Filed: May 12, 1982

[30] Foreign Application Priority Data

May 21, 1981 [NL] Netherlands .......................... 8102514

[51] Int. Cl.$^3$ ...................... A61K 35/14; C08B 37/10
[52] U.S. Cl. ................................... 424/183; 424/180; 536/21; 536/55.1; 536/55.2; 536/123
[58] Field of Search .................. 424/183, 180; 536/21, 536/55.1, 55.2

[56] References Cited

U.S. PATENT DOCUMENTS

| | | | |
|---|---|---|---|
| 4,175,182 | 11/1979 | Schmer | 424/183 |
| 4,301,028 | 11/1981 | Bartl et al. | 424/183 |
| 4,301,153 | 11/1981 | Rosenberg | 424/183 |
| 4,303,651 | 12/1981 | Lindahl et al. | 424/183 |
| 4,351,938 | 9/1982 | Barnett | 424/183 |

*Primary Examiner*—Johnnie R. Brown
*Attorney, Agent, or Firm*—Abelman, Frayne & Rezac

[57] ABSTRACT

A new anti-thromboticum based on a mixture of oligo- and polysaccharides is provided. The invention also relates to methods for preparation thereof and to pharmaceutical compositions including the said anti-thromboticum.

The new product is of natural origin and can be obtained from mammal tissue, particularly intestinal mucous. The product is useful because of its high "benefit/risk" ratio (i.e. the ratio between the anti-thrombotic activity and the haemorrhagic activity).

8 Claims, 5 Drawing Figures

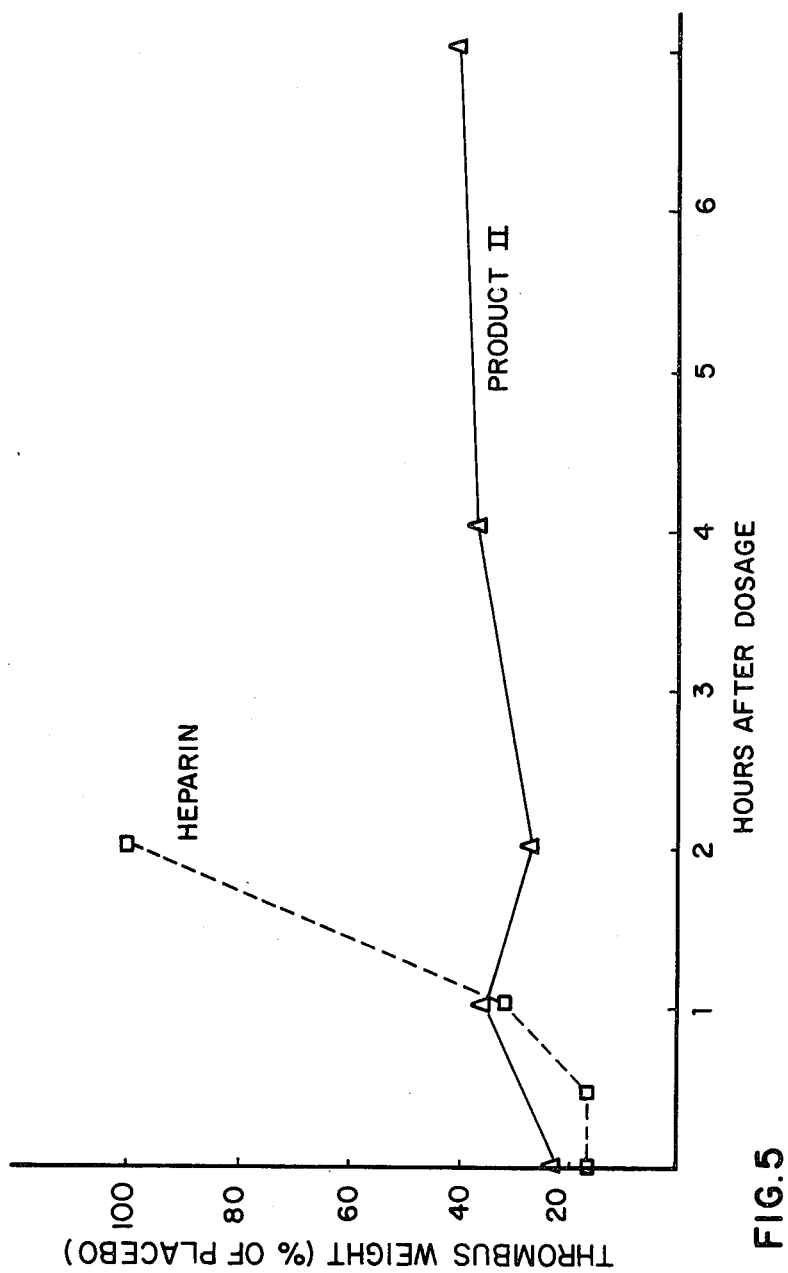

ANTI-THROMBOTICUM BASED ON POLYSACHARIDES, METHOD FOR ITS PREPARATION AND PHARMACEUTICAL COMPOSITIONS

The invention relates to a new anti-thromboticum based on a mixture of oligo- and polysaccharides and to methods for preparation thereof. The invention also relates to pharmaceutical compositions which include the said mixture.

It is known that certain mucopolysaccharides influence the coagulation properties of blood. The best known mucopolysaccharide is heparin, a sulphated mucopolysaccharide, which is employed in prophylaxis and the treatment of veinous thrombosis and thrombo-embolism. The anti-thrombotic effect of heparin is based on acceleration of the inhibition of blood-coagulating factors by anti-thrombin III. One major difficulty in using heparin for the prevention of and the therapy for thrombosis and thrombo-embolism is the bleeding inducing capacity of heparin. By optimising the dose, manner and frequency of application the risk of bleeding can to some extent be reduced, but the intrinsic ratio between the anti-thrombotic properties and the bleeding-inducing properties of heparin cannot be influenced.

In consequence thereof the prophylactic application of heparin has been restricted to those indications in which the coagulation system is activated only moderately, such as in the case of mild forms of deep vein thrombosis. A further short-coming of heparin is its relatively short period of action, so that for efficient prophylaxis, normally a dosage has to be administered at least twice per day.

Various attempts have already been made to produce "improved heparins", or to produce heparinoids with improved properties. For example, British patent publication No. 2 002 406 relates to an oligo-heteropolysaccharide mixture with a mol weight distribution between 2000 and 5000 daltons, which is obtained by depolymerisation of heparin and/or is isolated from the mother liquor of the normal heparin preparation, after which the material obtained is further sulphatised. It is stated that the ratio between the anti-thrombotic effect (in vivo activity) and anti-coagulation effect (in vitro activity) of the material thus obtained is more favourable than for heparin.

A new anti-thrombotically-effective heparinoid has now been discovered, which is a mixture of oligo- and heteropolysaccharides with a striking dissociation between the anti-thrombotic activity and the haemorrhagic activity (bleeding inducing capacity).

During various bleeding tests on rats (muscle bleeding test, capillary bleeding test) the new heparinoid appears to cause no bleeding or hardly any more bleeding than a placebo, whilst the haemorrhagic action over a wide dosage range (10–250 mg/kg) increased only to a slight extent. Admittedly the anti-thrombotic action per unit of weight is less than that of heparin, but the "benefit/risk" ratio (i.e. the ratio between the anti-thrombotic activity and the haemorrhagic activity) is 10–40 times more favourable than that of heparin. This will be illustrated below in further detail by means of comparative examples.

The new anti-thromboticum is of natural origin and consists of a mixture of oligo- and polysaccharides, which are based on hexose derivatives such as glucuronic acid, iduronic acid, glucosamine, galactosamine and sulphated and acetylated derivatives thereof. The new product is a white, amorphous, slightly hygroscopic powder having the following characteristics:

(a) a mol weight distribution (determined by comparison with dextran by means of gel permeation chromatography on a macroporous silica matrix (Nucleosil 50-5) with 0.5 molar ammonium acetate buffer (pH=5.0) as eluant) between 2000 and 40,000 daltons with a main peak between 2500 and 15,000 daltons, more specifically between 4,000 and 10,000 daltons, and averaged between 5000 and 8000 daltons, and usually an auxiliary peak and/or shoulder in the range between 15,000 and 60,000 daltons, more specifically between 30,000 and 50,000 daltons, with an average molecular weight of roughly 40,000 daltons;

(b) a specific rotation ($[\alpha]_D^{20}$) between $+25°$ and $+80°$, more specifically between $+30°$ and $+70°$;

(c) a nitrogen content between 1.5 and 4% by weight, preferably between 2.5 and 3.5% by weight;

(d) a sulphur content between 5 and 7.5% by weight, preferably between 5.5 and 6.5% by weight;

(e) a content of ionic groups in meq/g between 3 and 5, preferably between 3.5 and 4.5;

(f) a content of sulphamido groups in meq/g between 0.5 and 1.5, preferably between 0.5 and 1.0;

(g) a glucoseamine content in meq/g of 0.5 to 1.5;

(h) a galactosamine content in meq/g of 0.0 to 0.6; and (i) an idose (iduronic acid)/glucose (glucuronic acid) ratio of 0.5 to 3, more especially from 1 to 3.

Even though it is not possible to exactly specify the oligo- and polysaccharide composition of the new product, the above-mentioned parameters do characterise the product to a satisfactory extent, particularly in conjunction with its pharmacological profile.

The pharmacological profile of the new heparinoid is characterised by:

(1) an anti-coagulation activity (USP) of less than 10 international units per mg (IU/mg), thus only a fraction (usually less than 5%) of that of heparin USP;

(2) a negligible anti-thrombin activity (less than 1% of that of heparin USP);

(3) an anti-$X_a$ activity of less than 20% of that of heparin, usually between 2.5 and 15%;

(4) an anti-thrombotic activity (Umetsu model) with a ID$_{50}$ of roughly 2 to 8 mg/kg i.v. (ID$_{50}$ of heparin USP is roughly 0.4 to 0.5 mg/kg i.v.);

(5) a bleeding activity which scarcely increases over a wide dosage range (up to 300 mg/kg i.v.), whilst that of heparin USP at a dosage of 1 mg/kg i.v. is clearly observable and increases rapidly with higher dosages;

(6) a benefit/risk ratio which is 10–40 times more favourable than that for heparin USP having regard to the anti-thrombotic activity compared with the haemorrhagic activity; and (7) a half-value time which is certainly twice as long as that of heparin USP.

This interesting profile renders the new product extremely suitable for the prophylaxis and treatment of veinous thrombosis and thrombo-embolism. This product appears particularly suitable above all for the prevention of DVT (deep vein thrombosis) in patients who are being subjected to or have undergone hip surgery. Hitherto no adequate prophylactic measures have been feasible against the frequent occurrence of DVT and lung embolisms in the case of hip surgery. Low doses (s.c.) of heparin are not effective and higher i.v. doses are contra-indicated because of the high risk of bleeding.

The new product appears to possess no mutagenic and no toxic properties, even at high doses (up to 400 mg/kg/day).

The new product can be obtained in different ways. Mammal tissue such as lungs, pancreas, liver, intestines and particularly intestinal mucous can serve as the basic material. From the mammal tissue the product is initially liberated by autolysis or with the aid of proteolytic enzymes (e.g. enzymes from pig pancreas or bacterial enzymes, such as proteases from *Bacillus subtilis*). The product is subsequently isolated by precipitation with organic solvents, usually by means of solvents miscible with water, such as alcohols, e.g. methanol. Other methods of isolation are the binding of the product to a quaternary aliphatic ammonium base or a basic ion exchanger and subsequent elution of the product with aqueous salt solutions. Further purification of the product can be undertaken by fractional precipitation.

More detailed investigations have shown that by treating the product obtained in this manner with chondroitinase ABC, the greatest proportion of the high-molecular galactosamine-containing polysaccharides present is removed. The remaining product (about 70 to 75% of the initial product) however appears to have almost the same surprising pharmacological profile as the untreated product, in other words as a result of the said enzymatic treatment a preponderantly high-molecular inactive fraction (25-30% by weight) is removed.

The physical properties of this product obtained after treatment with chondroitinase ABC remain within the characteristics specified above for the new heparinoid, except that in the mol weight distribution the peak and/or shoulder of the high-molecular fraction has almost disppeared, the specific rotation appears to be increased to a value between $+45°$ and $+75°$, and the galactosamine content is reduced practically to zero. It is clear that the invention also comprises this product.

The new product(s) can be processed in the manner conventionally employed for heparin into a pharmaceutical dosage form, e.g. by dissolution in water suitable for injection purposes, to which if required further pharmaceutically acceptable auxiliary substances are added (preservation agent, certain salts). Clinical application is by means of subcutaneous or intraveinous (possibly intermittent) injection or by infusion. Other methods of dosing are also possible, such as intra-pulmonary application via spray inhalation or administration by means of a suppository.

The invention will be described in greater detail by means of the following examples without these restricting its scope.

EXAMPLE I

Bovine lung (100 kg) was treated with proteolytic enzymes from pig pancreas. After 15 hours incubation at pH 8.5, 40° C., the mixture was filtered off. The clear filtrate was brought into contact with a strongly basic ion exchanger (QAE Sephadex A50) and stirred for 15 hours. Then the ion exchanger was filtered off and eluted with an aqueous solution of NaCl (200 g/l). Methanol was added to the eluate up to 50% v/v. The resultant precipitate was removed, after which methanol was added to the mother liquor up to 75% v/v. The precipitate was recovered, washed with 100% methanol and dried. The white amorphous powder (22.7 g) obtained had a galactosamine content of 0.45 mmol/g, a glucosamine content of 0.54 mmol/g, an average molecular weight of 6600 daltons with an auxiliary peak at an average of 38,000 daltons (determined with respect to dextrane), a $[\alpha]_D^{20}$ of $+34.2°$, a sulphur content of 5.7%, a nitrogen content of 2.6%, a content of ionic groups of 3.90 meq/g, a content of sulphamido groups of 0.69 mmol/g and an idose/glucose ratio of 2.1.

Figure 1:
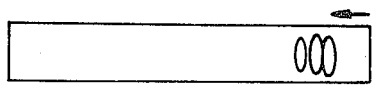

The product exhibited an electrophoresis pattern as shown in FIG. 1 (agarose gel, equilibrated in 0.2 molar calcium acetate, pH=7.2, buffer 0.2 molar calcium acetate; 300 V max., 7 mA, 30 minutes).

EXAMPLE II

Pig intestinal mucous (100 kg) was treated with proteases of *Bacillus subtilis* at 35° C. and pH 8.2 for 24 hours. The mixture was filtered and the clear filtrate was processed in a manner similar to that described in Example I. The yield was 3.2 g of white amorphous powder with a galactosamine content of 0.38 mmol/g, a glucosamine content of 0.82 mmol/g, an average molecular weight of 6100 daltons with an auxiliary peak at an average of 42,000 daltons (determined with respect to dextrane), an $[\alpha]_D^{20}$ of $+35.1°$, a sulphur content of 5.9%, a nitrogen content of 2.7%, a content of ionic groups of 3.70 meq/g, a content of sulphamido groups of 0.73 mmol/g and an idose/glucose ratio of 1.9.

The product exhibited a NMR spectrum (4% in $D_2O$ at 50° C., 270 MHz) as shown in FIG. 2.

EXAMPLE III

Bovine intestinal mucous (10 m$^3$) was processed with pancreatine (40° C., pH 8.5, 20 hours). The mixture was filtered and the filtrate processed in the manner as described in Example I. Yield 335 g of white amorphous powder with a galactosamine content of 0.28 mmol/g, a glucosamine content of 0.90 mmol/g, an average molecular weight of 5600 daltons with an auxiliary peak at on average 41,000 daltons (determined with respect to dextrane), a $[\alpha]_D^{20}$ of $+36.9°$, a sulphur content of 6.1%, a nitrogen content of 2.8%, a content of ionic groups of 4.0 meq/g, a content of sulphamide groups of 0.75 mmol/g and an idose/glucose ratio of 1.8.

EXAMPLE IV

The product from Example III (100 g) was treated with chondroitinase ABC. Via methanol precipitation (50-75% v/v) the remaining product was isolated. 72 g of product was obtained (white amorphous powder) with a galactosamine content of 0.05 mmol/g, a glucosamine content of 1.20 mmol/g, an average molecular weight of 5400 daltons with an extremely small auxiliary peak at on average 40,000 daltons (determined with respect to dextrane), a $[\alpha]_D^{20}$ of $+61.2°$, a sulphur content of 6.2%, a nitrogen content of 2.75%, a content of ionic groups of 4.1 meq/g, a content of sulphamido groups of 0.91 mmol/g and an idose/glucose ratio of 1.9.

Pharmacological tests

The products obtained in Examples I to IV were subjected to a number of pharmacological tests in comparison with heparin USP.

| | Influence on blood coagulation | | |
| --- | --- | --- | --- |
| Product | Anti-coagulation activity (IU/mg) | Anti-thrombin-activity (IU/mg) | Anti-$X_a$ activity (IU/mg) |
| heparin | 179 | 164 | 167 |
| Example I | 1 | 0.5 | 4.5 |
| Example II | 1 | 0.1 | 5 |
| Example III | 3 | 1.0 | 6 |
| Example IV | 4 | 1.3 | 8 |

The anti-coagulation activity was determined in accordance with the USP method. The anti-thrombin activity and the anti-$X_a$ activity were ascertained using a chromogenic substrate method, whereby purified cow anti-thrombin III and the substrates (Kabi AB, Sweden) S-2238 and S-2222 respectively were employed.

Anti-thrombotic activity

Anti-thrombotic activity was determined in the Umetsu model (Thrombos. Haemostas. 39, 74–83, 1978) in rats. In this model thrombi are made to occur in arterio-veinous shunts by allowing blood to flow along a silken thread for 15 minutes. The placebo effect and the influence of the substances to be tested in differing doses on thrombus formation is measured. From the relationship between dose and the inhibition of thrombus formation with respect to the placebo effect it is possible to derive a $ID_{50}$ (dose required for 50% inhibition of the thrombus formation).

| | Results |
| --- | --- |
| Product | $ID_{50}$ in mg/kg |
| heparin USP | 0.5 |
| Example I | 6.0 |
| Example II | 5.0 |
| Example III | 4.0 |
| Example IV | 5.3 |

Haemorrhagic activity (a) Capillary bleeding test in rats

Placebo or the products to be tested were dosed via the dorsal vein of the penis of anaesthetised rats. After one minute a strip of skin was pulled away manually from the shaven abdomen along two previously applied incisions. The wound was covered with a gauze bandage and the strip of skin was laid back over the gauze. After 10 minutes the gauze was removed and the blood present therein was extracted with 20 ml of water. The haemoglobin concentration in the water was measured spectrophotometrically and employed as parameter for the loss of blood (see Thrombos. Haemostas. 42, 466, 1979).

Figure 3:
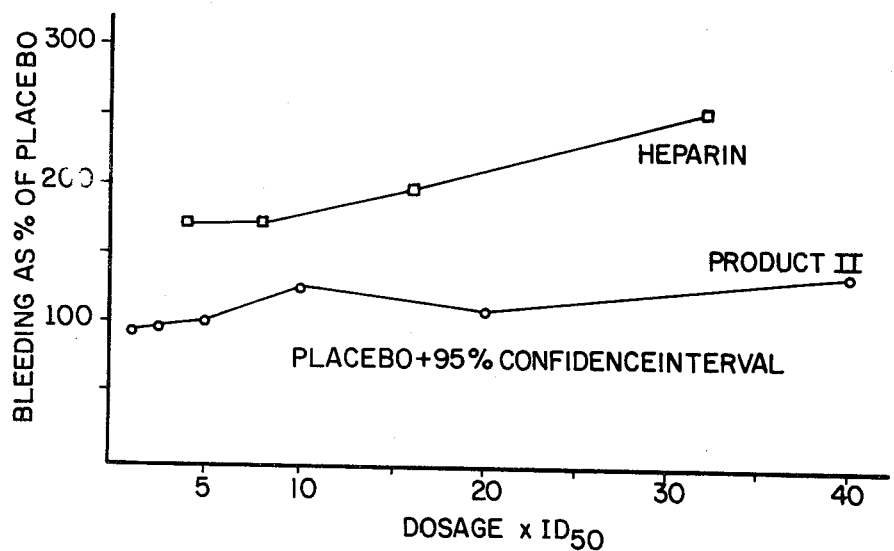

During this test the product from Example II and heparin were compared at different dosages, consideration being given to the difference in anti-thrombotic activity as between the new product and heparin. The result is shown in FIG. 3. Corresponding results were obtained with the products from Examples I, III and IV.

(b) Muscle bleeding tests in rats

Figure 4:
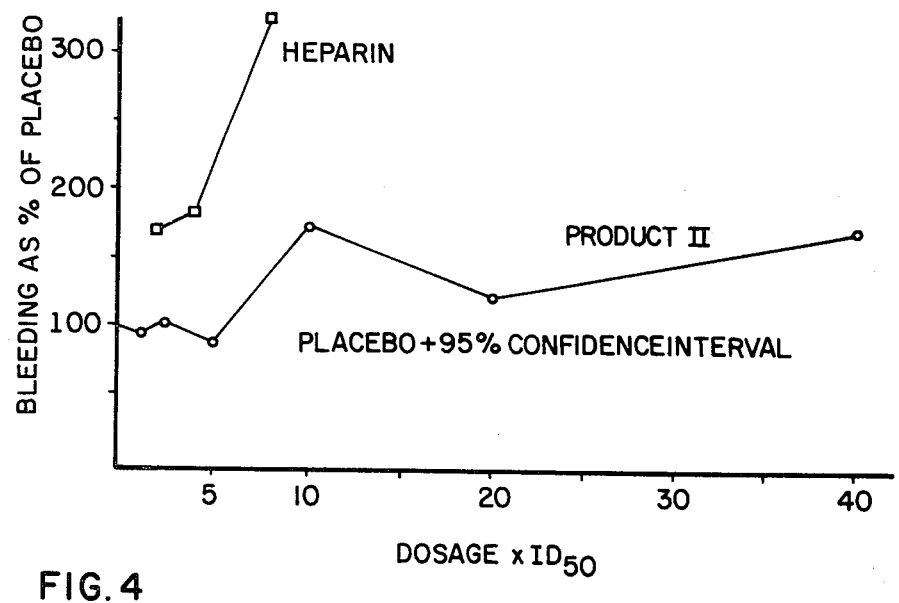

The biceps femoris in each paw of an anaesthetised rat was out longitudinally with a scalpel, one minute after the placebo or product to be tested had been administered intravenously via the dorsal vein of the penis. Each wound was covered with a gauze bandage. After 30 minutes the bandages were removed. The loss of blood was determined in the same way as during the capillary bleeding test. The product from Example II and heparin were compared in this test. The result is shown in FIG. 4. Corresponding results were obtained with the products from Examples I, III and IV.

FIGS. 3 and 4 show clearly the much greater tendency towards bleeding of heparin, whilst that of the new product does not differ or hardly differs significantly at all from that of the placebo over a wide dosage range. The benefit/risk ratio is quite obviously in favour of the new product.

Half-value time anti-thrombotic effect

The duration of the anti-thrombotic effect was determined in the Umetsu model for heparin and for the product from Example II, whereby heparin and the new product were tested in the ratio of their $ID_{50}$ (heparin 2 mg/kg i.v., product II, 20 mg/kg i.v.). The result is shown in FIG. 5.

The new product is obviously effective for a longer period than heparin. Corresponding results were obtained with the products from Examples I, III and IV.

We claim:

1. An antithrombotically effective heparinoid, which is a mixture of oligo- and polysaccharides from residues of glucuronic acid, iduronic acid, glucosamine, galactosamine, and sulfated and acetylated derivatives thereof, said heparinoid having
   (a) a molecular weight between 2000 and 40,000 daltons with a main peak between 2500 and 15,000 daltons and an auxiliary peak and/or shoulder in the range between 15,000 and 60,000 daltons;
   (b) a specific rotation ($[\alpha]_D^{20}$) between $+25°$ and $+80°$;
   (c) a nitrogen content between 1.5 and 4% by weight;
   (d) a sulphur content between 5 and 7.5% by weight;
   (e) a content of ionic groups in meq/g between 3 and 5;
   (f) a content of sulphamido groups in meq/g between 0.5 and 1.5;
   (g) a glucosamine content in meq/g of 0.5 to 1.5;
   (h) a galactosamine content in meq/g of 0.0 to 0.6;
   (i) an idose (iduronic acid)/glucose (glucuronic acid)-ratio of 0.5 to 3;
   said heparinoid having
   (1) an anti-coagulation activity (USP) of less than 10 international units per mg;
   (2) a negligible thrombin activity (less than 1% of that of heparin USP);
   (3) an anti-$X_a$ activity of less than 20% of that of heparin, usually between 2.5 and 15%;
   (4) an anti-thrombotic activity (Umetsu model) with an $ID_{50}$ of roughly 2 to 8 mg/kg i.v.;
   (5) a bleeding activity which hardly increases at all over a wide dosage range (up to 300 mg/kg i.v.);
   (6) a benefit/risk ratio which is 10–40 times more favourable than that for heparin USP having regard to the anti-thrombotic activity as compared with haemorrhagic activity, and
   (7) half value time which is at least twice as long as that of heparin USP.

2. Pharmaceutical composition having anticlotting activity which comprises an anticlotting effective amount of a compound of claim 1 in a pharmaceutically acceptable carrier.

3. An antithrombotically effective heparinoid, which is a mixture of oligo- and polysaccharides from residues of glucuronic acid, iduronic acid, glucosamine, galactosamine, and sulfated and acetylated derivatives thereof, said heparinoid having
  (a) a molecular weight between 2000 and 40,000 daltons with a main peak between 2500 and 15,000 daltons;
  (b) a specific rotation ($[\alpha]_D^{20}$) between +25° and +80°;
  (c) a nitrogen content between 1.5 and 4% by weight;
  (d) a sulphur content between 5 and 7.5% by weight;
  (e) a content of ionic groups in meq/g between 3 and 5;
  (f) a content of sulphamido groups in meq/g between 0.5 and 1.5;
  (g) a glucosamine content in meq/g of 0.5 to 1.5;
  (h) a galactosamine content in meq/g of 0.0 to 0.1; and
  (i) an idose (iduronic acid)/glucose (glucuronic acid)-ratio of 0.5 to 3;
said heparinoid having
  (1) an anti-coagulation activity (USP) of less than 10 international units per mg;
  (2) a negligible thrombin activity (less than 1% of that of heparin USP);
  (3) an anti-$X_a$ activity of less than 20% of that of heparin, usually between 2.5 and 15%;
  (4) an anti-thrombotic activity (Umetsu model) with an $ID_{50}$ of roughly 2 to 8 mg/kg i.v.;
  (5) a bleeding activity which hardly increases at all over a wide dosage range (up to 300 mg/kg i.v.);
  (6) a benefit/risk ratio which is 10–40 times more favourable than that for heparin USP having regard to the anti-thrombotic activity as compared with haemmorrhagic activity, and
  (7) half value time which is at least twice as long as that of heparin USP.

4. An antithrombotically effective heparinoid, which is a mixture of olgio- and polysaccharides from residues of glucuronic acid, iduronic acid, glucosamine, glaactosamine, and sulfated and acetylated derivatives thereof, said heparinoid having
  (a) a molecular weight between 2000 and 40,000 daltons with a main peak between 4000 and 10,000 daltons and an average molecular weight of between 5000 and 8000 daltons and an auxiliary peak and/or shoulder in the range between 30,000 and 50,000 daltons with an average molecular weight of about 40,000 daltons;
  (b) a specific rotation ($[\alpha]_D^{20}$) between +40° and +70°;
  (c) a nitrogen content between 2.5 and 3.5% by weight;
  (d) a sulphur content between 5.5 and 6.5% by weight;
  (e) a content of ionic groups in meq/g between 3.5 and 4.5;
  (f) a content of sulphamido groups in meq/g between 0.5 and 1.5;
  (g) a glucosamine content in meq/g of 0.5 to 1.5;
  (h) a galactosamine content in meq/g of 0.0 to 0.6;
  (i) an idose (iduronic acid)/glucose (glucuronic acid)-ratio of 1.0 to 3;
said heparinoid having
  (1) an anti-coagulation activity (USP) of less than 10 international units per mg;
  (2) a negligible thrombin activity (less than 1% of that of heparin USP);
  (3) an anti-$X_a$ activity of less than 20% of that of heparin, usually between 2.5 and 15%;
  (4) an anti-thrombotic activity (Umetsu model) with an $ID_{50}$ of roughly 2 to 8 mg/kg i.v.;
  (5) a bleeding activity which hardly increases at all over a wide dosage range (up to 300 mg/kg i.v.);
  (6) a benefit/risk ratio which is 10–40 times more favourable than that for heparin USP having regard to the anti-thrombotic activity as compared with haemorrhagic activity; and
  (7) half value time which is at least twice as long as that of heparin USP.

5. An antithrombotically effective heparinoid, which is a mixture of oligo- and polysaccharides from residues of glucuronic acid, iduronic acid, glucosamine, galactosamine, and sulfated and and acetylated derivatives thereof, said heparinoid having
  (a) a molecular weight between 2000 and 40,000 daltons with a main peak between 4000 and 10,000 daltons and an average molecular weight of between 5,000 and 8,000 daltons;
  (b) a specific rotation ($[\alpha]_D^{20}$) between +40° and +70°;
  (c) a nitrogen content between 2.5 and 3.5% by weight;
  (d) a sulphur content between 5.5 and 6.5% by weight;
  (e) a content of ionic groups in meq/g between 3.5 and 4.5;
  (f) a content of sulphamido groups in meq/g between 0.5 and 1.5;
  (g) a glucosamine content in meq/g of 0.5 to 1.5;
  (h) a galactosamine content in meq/g of 0.0 to 0.1; and
  (i) an idose (iduronic acid)/glucose (glucuronic acid)-ratio of 1.0 to 3;
said heparinoid having
  (1) an anti-coagulation activity (USP) of less than 10 international units per mg;
  (2) a negligible thrombin activity (less than 1% of that of heparin USP);
  (3) an anti-$X_a$ activity of less than 20% of that of heparin, usually between 2.5 and 15%;
  (4) an anti-thrombotic activity (Umetsu model) with an $ID_{50}$ of roughly 2 to 8 mg/kg i.v.;
  (5) a bleeding activity which hardly increases at all over a wide dosage range (up to 300 mg/kg i.v.);
  (6) a benefit/risk ratio which is 10–40 times more favourable than that for heparin USP having regard to the anti-thrombotic activity as compared with haemorrhagic activity, and
  (7) half value time which is at least twice as long as that of heparin USP.

6. Pharmaceutical composition having anticlotting activity which comprises an anticlotting effective amount of a compound of claim 3 in a pharmaceutical acceptable carrier.

7. Pharmaceutical composition having anticlotting activity which comprises an anticlotting effective amount of a compound of claim 4 in a pharmaceutical acceptable carrier.

8. Pharmaceutical composition having anticlotting activity which comprises an anticlotting effective amount of a compound of claim 5 in a pharmaceutical acceptable carrier.

* * * * *